United States Patent [19]

Carr et al.

[11] 4,269,987
[45] May 26, 1981

[54] PURIFICATION OF TRIAZOLES

[75] Inventors: Richard P. Carr; Ashok K. Nanda, both of Cincinnati, Ohio; Charles A. Schneider, Villa Hills, Ky.; Girish K. Malhotra, Cincinnati, Ohio

[73] Assignee: The Sherwin-Williams Company, Cleveland, Ohio

[21] Appl. No.: 48,530

[22] Filed: Jun. 13, 1979

[51] Int. Cl.$^3$ .................. C07D 249/16; C07D 249/18
[52] U.S. Cl. ...................................... 548/257; 548/108
[58] Field of Search ......................................... 548/257

[56] References Cited

U.S. PATENT DOCUMENTS 3,564,001  2/1971  Long ................................. 548/257

Primary Examiner—Paul M. Coughlan, Jr.
Attorney, Agent, or Firm—John C. Purdue

[57] ABSTRACT

A method for purifying a triazole composition is disclosed. The method involves the steps of producing a substantially anhydrous slurry in an alcohol of an alkali metal or of an alkaline earth metal salt of the triazole to be purified, separating solids from the slurry and washing the solids with an alcohol. A preferred method includes the steps of charging to a suitable vessel a crude triazole, a substantially equivalent amount of sodium hydroxide, added to an aqueous solution, hexanol or another alcohol having comparatively low water solubility, and xylene or another inert solvent; water is then removed from the system by azeotropic distillation to produce the desired slurry. When the triazole is benzotriazole or any given tolyltriazole isomer, the purified triazole can merely be recovered from the dried solvent system by filtration, washed (usually with a mixture of fresh solvent of the same identity as that from which it had been filtered) and dried. When the triazole to be purified is a blend of the 4- and 5-tolyltriazole isomers, a method for producing fractions enriched in each of the two isomers (subsequently defined) is also disclosed. This latter method involves all of the steps described above, including recovery of the precipitate, washing and drying; in this instance, the precipitate is found to be substantially enriched, by comparison with the isomer mixture charged, in 5-tolyltriazole, while most of the 4-tolyltriazole remains dissolved in the filtrate.

7 Claims, 2 Drawing Figures

KEY:
5-TT MEANS 5-TOLYLTRIAZOLE
4-TT MEANS 4-TOLYLTRIAZOLE

PURIFICATION OF TRIAZOLES

DEFINITIONS

As used herein, the following terms have the meanings indicated below:

"Benzotriazole" means 1,2,3-benzotriazole:

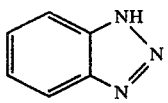

"4-tolyltriazole" means methyl substituted benzotriazole where the methyl group is in the 4 position:

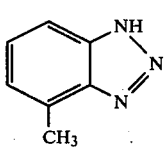

"5-tolyltriazole" means a methyl substituted benzotriazole where the methyl group is in the 5 position:

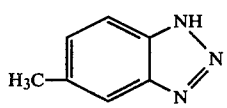

"Tolyltriazole" means a methyl substituted benzotriazole where the methyl substituent is in either of the 4- and 5- positions:

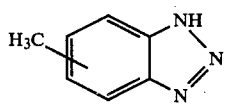

BACKGROUND OF THE INVENTION

The production of benzotriazole is disclosed in U.S. Pat. Nos. 2,861,078 to Miller et al, 3,227,726 to Levy and in 3,564,001 to Long. The Miller et al patent also discloses the production of various substituted triazoles, including both of the tolyltriazole isomers, and the purification of triazoles by carbon treatment. Both Levy and Long disclose the purification of triazoles by vacuum distillation.

It has also been suggested that benzotriazole of a lower degree of purity than is ultimately desired in antifreeze can be dissolved in ethylene glycol and co-distilled therewith, presumably effecting a purification of both the benzotriazole and the ethylene glycol.

BRIEF DESCRIPTION OF THE INVENTION

The present invention is based upon the discovery that a triazole composition can be purified by forming a substantially anhydrous slurry of a sodium or other salt of the triazole to be purified, separating solids from the slurry, and washing the solids with an alcohol. It has also been discovered, when the triazole composition purified as described in the preceding paragraph is a mixture of 4-tolyltriazole and 5-tolyltriazole, the precipitate recovered as described in the preceding paragraph has been enriched considerably in the 5-tolyltriazole, while the major portion of the 4-tolyltriazole remains in solution in the alcohol or, preferably, in a solution of the alcohol in an inert solvent such as xylene, hexane, or the like. A second triazole fraction can be recovered from the filtrate, after recovery of the fraction enriched in 5-tolyltriazole, by adding thereto a quantity of water sufficient to dissolve the sodium or other salt of the 4-tolyltriazole, separating the aqueous phase from the organic phase, acidifying the aqueous phase, e.g., with a mineral acid to a pH of about 6 to cause a separation of the triazole from the water, either as an oil, if the temperature is sufficiently high, or as a precipitate if the temperature is sufficiently low. It is usually desirable that this recovered 4-tolyltriazole be further purified, either by crystallization or by the method of the present invention.

DESCRIPTION OF PREFERRED EMBODIMENTS

Figure 1:
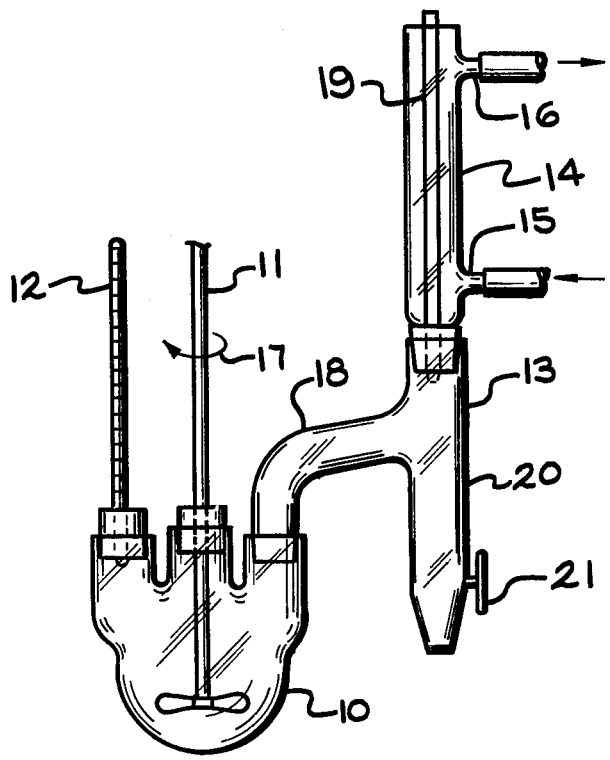
FIG. 1 is a view in vertical elevation of apparatus which is well suited for the production of a substantially anhydrous slurry in an alcohol of a sodium or other metal salt of a triazole to be purified.

The following Examples describe preferred embodiments of the present invention, Example 1 constituting the best presently known mode for practicing same, but are to be construed only as illustrating and disclosing, and not as limiting the invention.

EXAMPLE 1

An isomer blend of 4-tolyltriazole and 5-tolyltriazole was purified in a two liter, three-necked flask 10 (FIG. 1) equipped with a stirrer 11, a thermometer 12 and a Dean and Stark distillation head 13. The distillation head 13 was fitted with a reflux condenser 14 through which tap water at about 15° C. was circulated from an inlet 15 to an outlet 16. The charge to the flask 10 was made up of 130 g of tolyltriazole crude oil, 287 ml of xylene, 72 ml of technical grade hexanol (an isomer mix) and 74 g of 50 weight percent aqueous sodium hydroxide solution. After the flask 10 had been charged, rotation of the stirrer 11 in the direction of an arrow 17 was commenced to agitate the contents; a heating mantle (not illustrated) was applied to the flask 10; and circulation of cooling water through the reflux condenser 14 was commenced. Agitation of the contents of the flask 10 by the stirrer 11 was continued throughout a subsequently described distillation cycle. Heat was applied to the flask 10 by the mantle (not illustrated) to cause reflux of the charge. Vapors from the flask 10 passed through an arm 18 of the head 13 and into a central tube 19 of the reflux condenser 14. The vapors, in this case an azeotrope of hexanol and water, were condensed in the tube 19 and dripped into a dependent leg 20 of the head 13. Condensate was allowed to collect in the leg 20 by leaving a stopcock (not illustrated) controlled by a handle 21 in a closed position. Because hexanol and xylene are substantially insoluble in, and lighter than, water, the condensate consisted of a lower layer of water and an upper layer of a hexanol-xylene solution. As the distillation progressed, the hexanol-xylene surface in the leg 20 of the head 13 became sufficiently high that hexanol and xylene flowed through the arm 18 back into the flask 10. When the upper surface of the water in the leg 20 neared a point where water would flow through the arm 18 back into the flask 10, the stopcock (not illustrated) was opened to drain water from the leg 20.

The temperature of the contents of the three-necked flask 10 was monitored as distillation progressed. When this temperature reached 130° C., which was subsequent to the last observation of water condensed in the tube 19 of the reflux condenser 14, heating was discontinued, and the contents of the flask 10 were allowed to cool to about 60° C. A white precipitate which had formed was separated from the mother liquor by filtration. The filter cake was washed with 250 ml of a mixed solvent composed of 1 part by volume of hexanol to 4 parts by volume of xylene, and was then dried under vacuum at 100° C. The precipitate amounted to 68.7 g of sodium tolyltriazole, 45 percent of theory based upon the crude tolyltriazole charged; the sodium tolyltriazole was found by gas chromotography to consist of substantially 95 percent of the 5 isomer and 5 percent of the 4 isomer, while the crude tolyltriazole originally charged to the three-necked flask 10 was composed of substantially 55 percent of the 5 isomer and 45 percent of the 4 isomer, in addition to tar-like color bodies. A solution of the product in an equal weight of distilled water had a Gardner color of 12.

The filtrate from the process described in the preceding paragraph was combined with the mixed solvent washings and charged to a separatory funnel, together with 400 ml of distilled water. After shaking, the separatory funnel was allowed to stand in an upright position until there was a clear separation of a lower aqueous phase and an upper organic phase; the aqueous phase was then withdrawn from the separatory funnel into a two liter beaker, and acidifed to a pH of 6 with dilute sulfuric acid. A tolyltriazole precipitate which formed was separated from the aqueous phase by filtration and purified by vacuum distillation. The recovery was 61.1 g of tolyltriazole, 47 percent of theory, based upon the initial charge of crude oil. The product was found by gas chromotography to be composed of substantially 86 percent of 4-tolyltriazole and 14 percent of 5-tolyltriazole.

Figure 2:
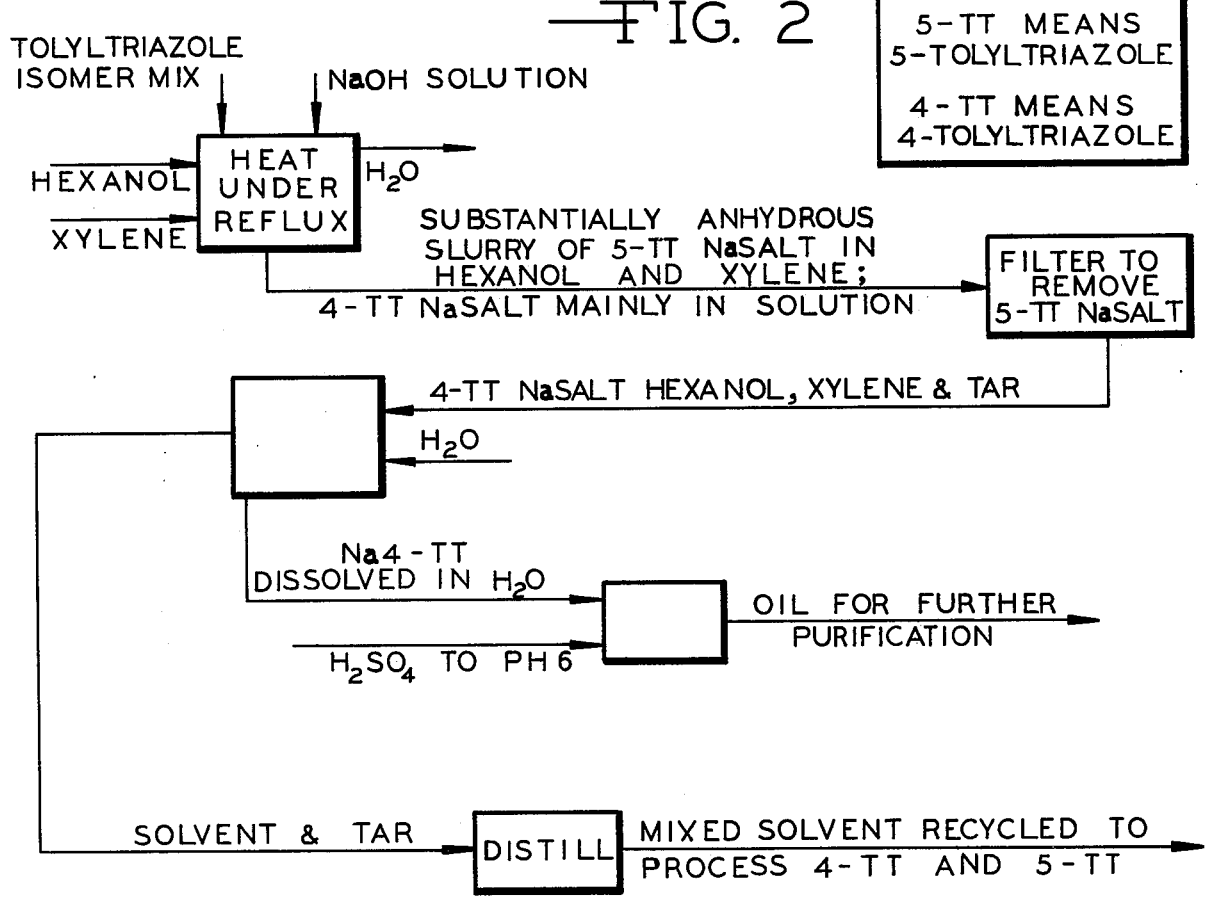
FIG. 2 is a flow diagram of the method of the present invention applied to the separation of 4-tolyltriazole from 5-tolyltriazole.

The procedure described in Example 1 is represented diagrammatically in FIG. 2 where the first step, characterized by the legend "Heat Under Reflux" is that carried out in the apparatus shown in FIG. 1, and described in connection therewith. The charge indicated in FIG. 2 is that described in Example 1. The purpose of this step is to produce a substantially anhydrous slurry, in the context of Example 1, of the sodium salt of 5-tolyltriazole in hexanol, xylene being used as a diluent, but also, as subsequently explained in more detail, facilitating the isomer separation reported in Example 1. More generally, the function of the first step is to produce a substantially anhydrous slurry of an alkali metal salt or of an alkaline earth metal salt of a triazole, usually benzotriazole, a tolyltriazole or a blend of tolyltriazole isomers, in an alcohol. The specific identity of the alcohol is not critical, although certain alcohols have properties which make their use clearly preferable over the use of other alcohols. Ethanol, for example, is a comparatively undesirable alcohol to use because it is miscible with water in all proportions, is lower boiling than water, and is difficult to separate substantially completely from water by distillation. However, even ethanol can be employed by charging absolute ethanol to the flask 10, together with the triazole to be purified and the sodium hydroxide solution; the amount of absolute ethanol charged must be sufficient that the ethanol in the flask 10 constitutes more than 95.5 percent by weight, based upon the total of ethanol and water. Furthermore, additions of absolute ethanol must be made as distillation progresses to maintain the ethanol concentration above the stated limit. The distillate, then, is the azeotropic mixture of ethyl alcohol and water containing 95.5 percent by weight of ethanol and 4.5 percent by weight of water. The azeotrope is condensed in the reflux condenser 14, and collects in the leg 20. There is, however, no visual check that the system has become substantially anhydrous because, when this occurs, the distillate is ethanol rather than the azeotropic mixture. As a consequence of the miscibility in all proportions of ethanol and water the appearance of the liquid in the leg 20 does not change when the system becomes anhydrous; because ethyl alcohol, at 760 mm, boils at 78.4° C. while the azeotrope boils at 78.1° C., there is no appreciable temperature change to indicate the anhydrous condition.

Hexanol is the best presently known alcohol for use in practicing the method of the invention, isobutanol ranking second, butanol third and ethyl hexanol fourth. Technical grade hexanol and pentanol, both of which are isomer mixtures, as distinguished from any single isomer, have been found to be entirely satisfactory. In general, $C_4$ to $C_8$ aliphatic alcohols are preferred; most desirably, the alcohol should have a boiling point not greater than 180° C.

In the Example 1 procedure, the xylene served as a diluent, keeping the contents of the flask 10 sufficiently fluid that they could be stirred as water distillation progressed; in addition, however, the xylene contributed to the purification, probably because the tar-like color bodies which contaminated the crude tolyltriazole charged had a higher solubility in the xylene than in the hexanol. Accordingly, it is preferred, particularly where a separation of the 4- and 5-tolyltriazole isomers is desired, to use a solvent system composed of an alcohol and a second solvent. The second solvent must be inert in the environment of the purification, i.e. when heated to temperatures up to about 150° C. and in the presence of alcohols, water, acid and triazoles. The preferred solvents are aprotic organic solvents, and can be aliphatic, aromatic or mixed aliphatic and aromatic solvents having melting points not greater than 50° C. The most desirable second solvents are benzene, toluene, xylene and aliphatic hydrocarbons having from 5 to 15 carbon atoms, including cycloaliphatic hydrocarbons, e.g. methyl cyclohexane and, in any event, having a melting point not greater than 50° C.

Substantially the procedure of paragraphs 1 and 2 of Example 1 has been used with other solvent systems to purify the triazole isomer mixture described in Example 1 and to purify benzotriazole. In each case, the triazole recovered from the solvent system which included an alcohol and an aprotic solvent was washed with about 1.9 ml of the solvent system used for purification per gram of the crude triazole charged. The purification procedures and the results achieved are summarized in the following Tables wherein the abreviations "P" and "N.D." mean, respectively, principally and not determined, while a plus or a minus symbol following a Gardner color designation means that the test solution was slightly more or less colored than the Gardner standard indicated, and "Id." means identity:

| Example | Triazole Id. | Amount g | Alcohol Id. | Amount ml | Aprotic Solvent Id. | Amount ml | Base Identity (50% by weight of the base in H₂O unless otherwise indicated) | Amount g | Gardner color of purified triazole sodium salt in an equal weight of distilled water | Yield g | per-cent | Percent 4TT* | 5TT |
|---|---|---|---|---|---|---|---|---|---|---|---|---|---|
| 2 | TT crude oil | 135 | Isobutanol | 47** | Xylene | 425** | NaOH | 77 | 17–18 | 98.7 | 62.7 | 19.5 | 80.5 |
| 3 | TT crude oil | 130 | Pentyl alcohol*** | 96 | Xylene | 382 | NaOH | 74 | 11 | 67.6 | 44.6 | 0.9 | 99.1 |
| 4 | TT crude oil | 130 | Isobutanol | 96 | Xylene | 382 | NaOH | 74 | 14 | 70.9 | 46.8 | 1.6 | 98.4 |
| 5 | TT crude oil | 200 | 2-ethylhexanol | 147 | Xylene | 588 | NaOH | 114 | 16 | 145.2 | 62.3 | | P |
| 6 | Pure distilled TT | 200 | 2-ethyl hexanol | 257 | Xylene | 478 | NaOH | 114 | N.D. | 117.9 | 50.6 | 2.0 | 98.0 |

*"TT", as used in this Table, means tolyltriazole.
**The initial solvent charge was 37 ml of isobutanol and 335 ml of xylene; when most of the water had been distilled an additional charge of 90 ml of xylene and 10 ml of isobutanol was added to the flask to facilitate stirring.
***An isomer blend.

A comparison of the results reported in the foregoing Table for Examples 2 and 4 indicates that increasing the proportion of xylene and decreasing the proportion of isobutanol, relative to those used in Example 4, caused an increase in the yield of purified product, but at the expense of purity as indicated both by Gardner color and proportion of isomers.

The purified product of Example 6 was dissolved in distilled water at about 85° C.; the resulting solution was acidified with dilute sulfuric acid to a pH of 6.0 and cooled. Upon acidification, an oily organic phase appeared. The oily phase crystallized at approximately 20° C., and was recovered by filtration and dried under vacuum at about 100° C. The yield was 98 g of a product which was found by gas chromatography to be composed of 98 percent 5-tolyltriazole and 2 percent of 4-tolyltriazole. The filtrate from Example 6, after separation of the purified product therefrom, was charged to a separatory funnel, together with substantially an equal volume of distilled water, and the funnel and contents were shaken. The funnel was then placed in a substantially vertical position until there was a clear separation of an upper organic phase and a lower aqueous phase; the lower aqueous phase was withdrawn from the separatory funnel and acidified with dilute sulfuric acid to a pH of about 6 to cause formation of a precipitate. The precipitate was separated from the aqueous phase by filtration, washed with distilled water and dried at about 100° C. The yield was 71.2 g of a mixture which was found by gas chromotography to be composed of 85.8 percent 4-tolyltriazole and 14.2 percent 5-tolyltriazole.

The filtrate from the process summarized in Example 5 and substantially an equal volume of distilled water were charged to a separatory funnel, shaken, and allowed to stand until there was a clear separation of a lower aqueous phase from an upper organic phase. This washing operation was conducted at a temperature of about 85° C. The aqueous phase was then withdrawn from the separatory funnel, acidified to a pH of about 6 with dilute sulfuric acid, and allowed to cool. Upon acidification, an oily tolyltriazole separated from the water; as the composition cooled, the tolyltriazole solidified. The solidified product was separated from the aqueous phase by filtration, and was then subjected to vacuum distillation. The yield was 60 g of an isomer mixture composed of 84 percent 4-tolyltriazole and 16 percent 5-tolyltriazole.

Substantially the procedure of paragraphs 1 and 2 of Example 1 has been used to carry out other triazole purifications. In each case, the triazole recovered from the solvent system which included an alcohol and an aprotic solvent was washed with about 1.9 ml of the solvent system used for purification per gram of the crude triazole charged. Typical purification procedures and the results achieved are summarized in the following Table:

| Ex. | Triazole Id. | Amount g | Alcohol Id. | Amount ml | Aprotic Solvent Id. | Amount ml | Base Identity (50% by weight of the base in H₂O unless otherwise indicated) | Amount g | Gardner color of purified triazole salt in an equal weight of distilled water | Yield g | per-cent | Percent 4TT* | 5TT |
|---|---|---|---|---|---|---|---|---|---|---|---|---|---|
| 7 | TT crude | 260 | Hexanol | 144 | Xylene | 574 | NaOH | 148 | 9 | 141.6 | 46.8 | 99.0 | 1.0 |

-continued

| | Triazole | | Alcohol | | Aprotic Solvent | | Base Identity (50% by weight of the base in H2O unless otherwise indicated) | Amount g | Gardner color of purified triazole salt in an equal weight of distilled water | Yield | | Percent | |
|---|---|---|---|---|---|---|---|---|---|---|---|---|---|
| Ex. | Id. | Amount g | Id. | Amount ml | Id. | Amount ml | | | | g | per-cent | 4TT* | 5TT |
| 8 | TT crude oil | 130 | Hexanol | 72 | Benzene | 287 | NaOH | 74 | 9 | 72.0 | 47.5 | N.D. | N.D. |
| 9 | TT crude oil | 130 | Hexanol | 72 | Cyclohexane | 287 | NaOH | 74 | 14 | 74.6 | 49.2 | N.D. | N.D. |
| 10 | TT crude oil | 130 | Hexanol | 72 | Xylene | 287 | Ca(OH)2 | 34.4* | 18 | 75.0** | 57.7 | N.D. | N.D. |
| 11 | TT crude oil | 61.1 | Hexanol | 34 | Xylene | 134 | Ba(OH)2 . 5H2O | 115 | 15 | 29.0** | 47.5 | N.D. | N.D. |
| 12 | Pure distilled TT | 200 | 2-ethyl-hexanol | 147 | Xylene | 588 | NaOH | 114 | N.D. | 120.5** | 60.2 | 20 | 80 |
| 13 | BT crude oil | 130 | Hexanol | 72 | Xylene | 287 | NaOH | 83 | N.D. | 118.5 | 76.4 | — | — |
| 14 | TT crude oil*** | 60 | Hexanol | 33 | Xylene | 132 | MgO | 17.1* | | | | | |
| 15 | BT crude oil | 130 | Hexanol | 72 | Xylene | 287 | MgO | 21.8* | N.D. | 105.9 | 74.0 | — | — |

*Added in the anhydrous condition.
**Recovered as TT.
***No reaction occurred in this experiment; so far as is known, magnesium oxide is inoperable for practicing the present invention to purify TT.

What we claim is:

1. A method for purifying a benzo-/tolyl-triazole composition, which method includes the steps of producing a substantially anhydrous slurry in an alcohol of an alkali metal or of an alkaline earth metal salt of the triazole to be purified, with the proviso that the salt is not a magnesium salt when the triazole is a tolyl triazole, separating purified triazole salt solids from the slurry and washing the purified triazole salt solids with an alcohol.

2. A method as claimed in claim 1 wherein the alcohol in which the slurry is produced and with which the solids are washed is an aliphatic alcohol having from 4 to 8 carbon atoms and a vapor pressure of 760 mm Hg at a temperature not greater than 180° C.

3. A method as claimed in claim 2 wherein the anhydrous slurry additionally contains an inert aprotic organic solvent having a melting point not greater than 50° C. in an amount ranging from 10 percent to 90 percent, based upon the weight of the inert aprotic solvent and of the alcohol.

4. A method as claimed in claim 3 wherein the inert aprotic solvent is benzene, toluene, xylene or a cyclic or acyclic alkane having from 5 to 15 carbon atoms.

5. A method as claimed in claim 4 wherein the triazole purified is a blend of 4-tolyltriazole and 5-tolyltriazole and wherein, after solids are separated from the slurry, the filtrate is washed with water, the aqueous phase is separated from the organic phase and is acidified to precipitate a tolyltriazole, and the precipitate is separated from the aqueous phase.

6. A method as claimed in claim 4 wherein the substantially anhydrous slurry is produced by charging the triazole to be purified, a substantially equivalent amount of an alkali metal or alkaline earth metal hydroxide, water, an alcohol and an inert aprotic solvent to a distillation vessel and removing substantially all of the water from the charge by distillation.

7. A method as claimed in claim 6 wherein the solids separated from the slurry are reslurried in a solvent system having substantially the same composition as that used in producing the first slurry, and solids are then separated from the second slurry.

* * * * *